United States Patent [19]

Ando et al.

[11] Patent Number: 5,068,542
[45] Date of Patent: Nov. 26, 1991

[54] METHOD AND APPARATUS FOR CONCENTRATION MEASUREMENT BY THE QUANTITY, DIAMETER AND CONVERGENT OF A TRANSMITTED LIGHT BEAM

[75] Inventors: Minato Ando; Takashi Kato; Hideyasu Aoki; Yasuyuki Mizushima; Tsunetoshi Okura; Akemi Kurokawa, all of Nagoya, Japan

[73] Assignee: NGK Spark Plug Company, Ltd., Aichi, Japan

[21] Appl. No.: 540,606

[22] Filed: Jun. 19, 1990

[30] Foreign Application Priority Data

Jun. 22, 1989 [JP] Japan ................................ 1-160104

[51] Int. Cl.$^5$ ............................................ G01N 15/06
[52] U.S. Cl. ..................................... 250/573; 356/128
[58] Field of Search ................. 250/573, 574; 356/128, 356/133, 448

[56] References Cited

U.S. PATENT DOCUMENTS

| | | | |
|---|---|---|---|
| 3,950,104 | 4/1976 | Munk | 356/128 |
| 4,135,100 | 1/1979 | Harada et al. | 250/573 |
| 4,886,366 | 12/1989 | Kogure | 356/448 |
| 4,967,187 | 10/1990 | Dumas et al. | 250/573 |

Primary Examiner—David C. Nelms
Assistant Examiner—Que T. Le
Attorney, Agent, or Firm—Finnegan, Henderson, Farabow, Garrett, & Dunner

[57] ABSTRACT

A concentration measuring method and an apparatus measures the concentration of an objective solvent in a mixed solution by flowing a mixed solution through a tube, transmitting light through the mixed solution as it flows through the tubing and measuring the quantity of light transmitted through the fluid. The concentration of the objective solvent in the mixed solution is measured on the basis of either the quantity of light transmitted, the diameter of a light beam received, or a point of convergence of the light transmitted through the mixed solution. These factors being dependent on the concentration of the objective solvent in the mixed solution.

21 Claims, 5 Drawing Sheets

METHOD AND APPARATUS FOR CONCENTRATION MEASUREMENT BY THE QUANTITY, DIAMETER AND CONVERGENT OF A TRANSMITTED LIGHT BEAM

BACKGROUND OF THE INVENTION

1. Field of the Invention

The present invention relates to a method and apparatus for measuring the concentration of an objective solvent in a mixed solution. The present invention may be applied for process control in the chemical industry, the food industry and the medical and pharmaceutical industries, environmental measurement, medical diagnosis, etc.

2. Description of the Prior Art

Conventional methods of measuring the concentration of an objective solvent in a mixed solution are classified according to measurement of (1) an absorption spectrum, (2) the absorbency of the solution by coloring the objective solvent with a color coupler, (3) the electrical conductivity of the mixed solution, (4) the index of refraction of the mixed solution, and (5) the specific gravity of the mixed solution.

Methods (1), (3), (4), and (5) are not suitable for continuous measurement. Moreover method (1) needs a large measuring apparatus, method (2) is applicable only to the measurement of the concentration of a colorable objective solvent, and method (3) applies only to the measurement of the concentration of an objective solvent in an electrically conductive mixed solution.

SUMMARY OF THE INVENTION

An object of the present invention is a concentration measuring method and apparatus based on the fact that light traveling from one end to the other end of a tube filled with a flowing mixed solution converges on the axis of the tube.

Another object of the present invention is a concentration measuring method and apparatus applicable to continuous measurement in a wide range of applications which is not susceptible to electrical noise, variations of the luminous intensity of the light source, and accidental contamination by small bubbles, etc.

Yet another object of the present invention is a concentration measuring method and apparatus that is useful in remote process control.

Still another object of the present invention is a concentration measuring apparatus that is simple, inexpensive and of compact construction.

These and other objects of the present invention are accomplished by a concentration measuring method comprising the steps of flowing a mixed solution in a tube, transmitting light through one end of the tube, through the mixed solution in the tube, and out of the other end of the tube, as a light beam; detecting the quantity of light received, the diameter of the light beam, or a point of convergence of the light beam; and measuring the concentration of the objective solvent in the mixed solution on the basis that the quantity of light received, the diameter of the light beam received, or the point of convergence of the light beam. These factors are dependent on the concentration of the objective solvent in the mixed solution.

The above and other objects of the present invention are also achieved by a concentration measuring apparatus comprising a tube through which a mixed solution flows, feed means for feeding the mixed solution into a first end of the tube, discharge means for discharging the mixed solution from the other end of the tube, light emitting means disposed at the first end of the tube for emitting a light beam into the tube, and light detecting means at the second end of the tube for measuring the quantity of light received as the light beam, the diameter of the light beam received, or a point of convergence of the light beam through the mixed solution flowing in the tube.

BRIEF DESCRIPTION OF THE DRAWINGS

The manner by which the above and other objects, features, and advantages of the present invention are accomplished will be fully apparent from the following description taken in connection with the accompanying drawings, in which.

DETAILED DESCRIPTION OF THE PREFERRED EMBODIMENTS

When light is sent into one end of a tube filled with a flowing mixed solution, and is transmitted to the other end of the tube, the light converges on the axis of the tube even if the tube is not heated or cooled. The mode of convergence is dependent on the kind of solvent and mixing ratio of the mixed solution. Although the cause of the convergence of the light has not been fully elucidated, it may be empirically proven that the light converges when the mixed solution flows through the tube under prescribed conditions.

When the quantity of light transmitted through the mixed solution is measured by receiving the light on a light receiving area, for example, the area of the end face of an optical fiber, which is smaller than a minimum area of a light spot at a fixed position, the quantity of light or the point of convergence of the light is dependent on the concentration of the objective solvent in the mixed solution. Further, the diameter of the light beam spotted on the screen may be measured, the beam diameter being dependent on the concentration of the objective solvent in the mixed solution.

Accordingly, when the relation between the concentration of an objective solvent and the quantity of light received the point of convergence of the light beam, or the diameter of the light beam is determined beforehand for mixed solutions of various mixing ratios, the concentration of solvent can be determined by the measurement of the quantity of light received, etc.

According to the concentration measuring method and apparatus of the present invention, the quantity of light received exhibits a satisfactory relation, particularly a linear relation, with the concentration of an objective solvent in a mixed solution over a wide range of concentration. A combination of a simple optical system and a tube is used, and the concentration of an objective solvent of a mixed solution can be continuously measured with high reliability. Further, the concentration measuring method and apparatus of the present invention is not susceptible to pH and electric noise, and is able to measure the concentration stably. Furthermore, the concentration measuring method and apparatus of the present invention may be applicable to the measurement of substances which do not generate heat or do not absorb heat. Accordingly, the present invention has a wide range of applications. Moreover, measurement reliability does not depend on variations of the luminous intensity of the light source, accidental contamination by small bubbles, etc. Neither a highly accurate light receiving device nor a stable light source is required, so that a simple, inexpensive, and easy to construct and use system may be achieved.

Figure 1:
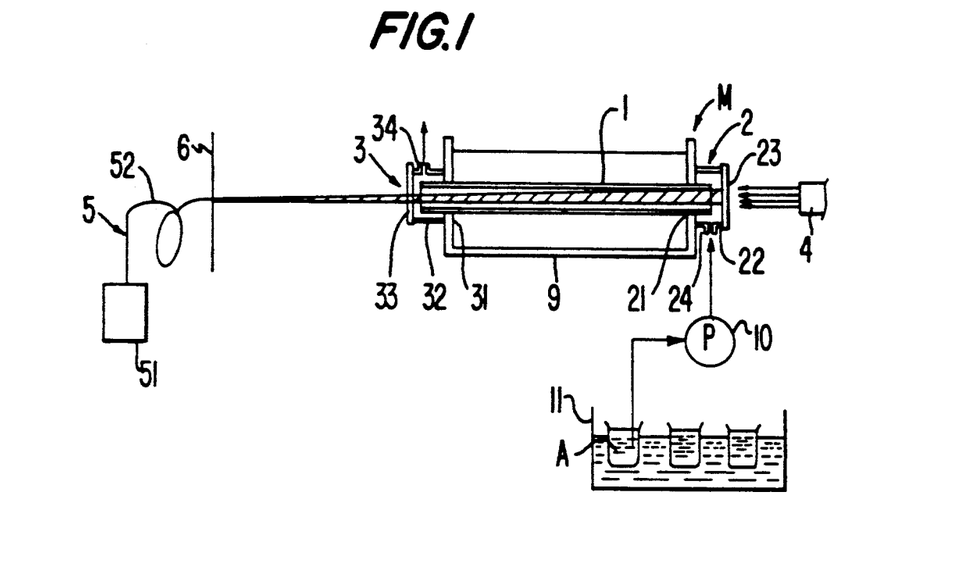
FIG. 1 is a schematic illustration of a concentration measuring apparatus according to a first embodiment of the present invention.

A concentration measuring apparatus according to the first embodiment of the present invention may be used for measuring the ethanol concentration of a water-ethanol mixed solution. As shown in FIG. 1, the concentration measuring apparatus comprises a light transmission module M, a He-Ne laser 4, a light quantity measuring unit 5, and a constant-temperature tank 9. The module M comprises a tube 1, an inlet unit 2 as feed means and an outlet unit 3 as discharge means.

The tube 1 may be a copper tube with an inside diameter of 2 mm, an outside diameter of 3 mm, and a length of 120 mm. The inlet unit 2 may comprise a base 21 disposed inside, a glass window (a light transmission window) 23 disposed outside, and a cylinder 22. The cylinder 22 is disposed between the base 21 and the glass window 23 and is attached to the base 21. An inlet port 24 may be attached to the side parts of the cylinder 22. The inlet unit 2 is detachably joined to one end of the tube 1.

The outlet unit 3 may comprise a base 31 disposed inside, a glass window (a light transmission window) 33 disposed outside, and a cylinder 32. The cylinder 32 is disposed between the base 31 and the glass window 33 and is attached to the base 31. An outlet port 34 may be attached to the side parts of the cylinder 32. The outlet unit 3 is detachably joined to the other end of the tube 1.

The bases 21 and 31 form parts of the constant-temperature tank 9. Further, the bases may separate from the end walls of the constant-temperature tank 9. A mixed solution (A) is fed through the inlet port 24 and is discharged through the outlet port 34. Further, the mixed solution (A) may be fed (or discharged) in the reverse direction. The junction of the tube 1 and the inlet unit 2, and that of the tube 1 and the outlet unit 3 are sealed with appropriate sealing members.

The He-Ne laser 4 is disposed opposite to the glass window 23 of the inlet unit 2, and a light quantity measuring unit 5 is disposed opposite to the glass window 33 of the outlet unit 3. The positions of the He-Ne laser 4 and the light quantity measuring unit 5 may be interchanged. According to the light quantity measuring unit 5, a screen 6 is disposed in a plane perpendicular to the axis of the tube 1 at a predetermined distance, e.g., about 2000 mm, from the glass window 33. An optical fiber 52 having a core diameter of 50 $\mu$m is disposed with its extremity substantially at the center of the screen 6, and an optical power meter 51 ([Anritsu ML-910B], Anritsu Co. Ltd.), is connected to the optical fiber 52. Further, the extremity of the optical fiber 52 may be inserted in the glass window 33 (or non-light transmission window).

The He-Ne laser 4 (e.g., wavelength: 543 nm and output power 1 mW) serves as a light source. The He-Ne laser 4 produces a laser beam and projects the laser beam through the glass window 23 into the tube 1 substantially in parallel to the axis of the tube 1. The laser beam transmitted through the mixed solution (A) flowing in the tube 1 is received by the optical power meter 51 through the optical fiber 52. The optical power meter 51 measures the quantity of the laser beam received by the optical fiber 52. The majority of the tube 1 is disposed within the constant-temperature tank 9 (e.g., 28° C.). The mixed solution (A) is contained in another constant-temperature tank 11 (e.g., 28° C.) and is fed through the inlet port 24 into the tube 1 by a pump 10.

Figure 2:
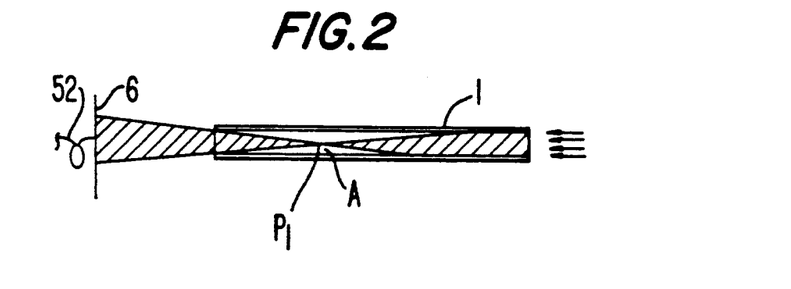
FIG. 2 is an explanatory illustration of the mode of convergence of light transmitted when ethanol is used as a medium in the first embodiment.
Figure 3:
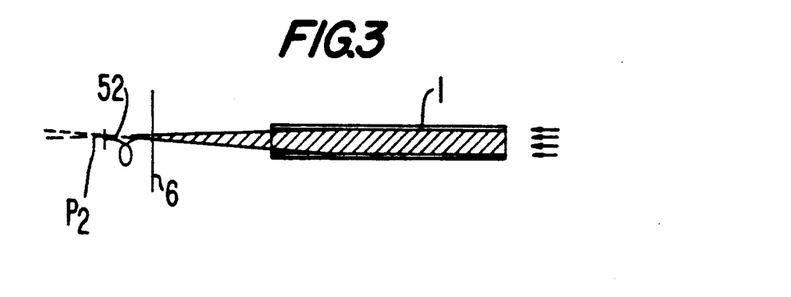
FIG. 3 is an explanatory illustration of the mode of convergence of light transmitted when water is used as a medium in the first embodiment.
Figure 4:
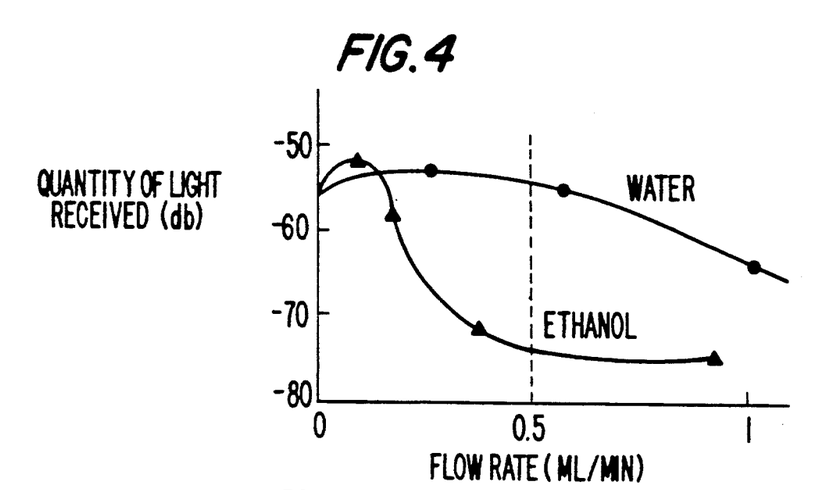
FIG. 4 is a graph showing the relation of the quantity of light received to flow rate for water and ethanol in the first embodiment.

The relations between flow rate and the quantity of light received, as predetermine individually for ethanol (guaranteed reagent) and pure water through experiments, are shown in FIG. 4. Further, the mode of convergence of light through ethanol is shown in FIG. 2, and the mode of convergence of light through water is shown in FIG. 3. As is obvious from FIG. 4, the quantity of light received varies with flow rate, and the relations for ethanol and pure water are different from each other. A desirable flow rate is 0.5 ml/min, at which the difference between the quantity of light received when ethanol is fed and that of light received when pure water is fed is a maximum.

In the present embodiment, the distance between the screen 6 and the glass window 33 is 2000 mm, which is selected as preferable for the purpose, but an optimum distance may be determined selectively in view of measuring conditions including the kind of a medium (solvent), and the flow rate, etc. When the mixed solution was not fed, the quantity of light received was −54 db and was regular, namely the quantity of light received did not show a satisfactory linear relation, therefore a good result was not achieved.

Figure 5:
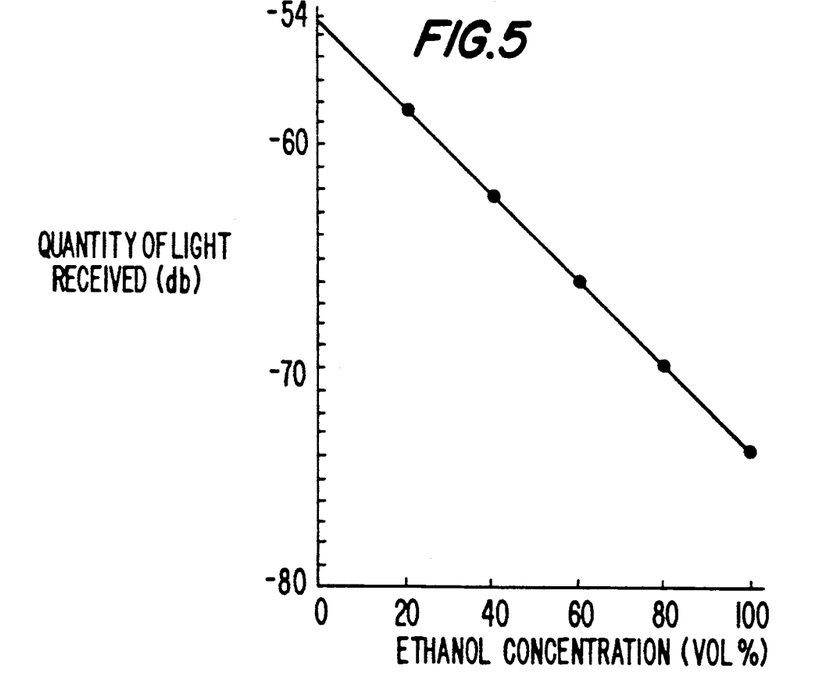
FIG. 5 is a graph showing the relation of the quantity of light received to ethanol concentration in the first embodiment.

Solutions of different mixing ratios were prepared and were maintained at 28° C. by the constant temperature tank 11. FIG. 5 shows the measured variation of the quantity of light received with ethanol concentration for those mixed solutions of different mixing ratios. As shown in FIG. 5, the concentration of ethanol and the quantity of light received had a satisfactory linear relation. When this analytical curve is used, and the quantity of light received through a mixed solution having an unknown ethanol concentration is measured, the unknown ethanol concentration can be readily determined. Accordingly when the ethanol concentration is measured by this apparatus, the ethanol concentration can be determined readily, accurately, quickly, and continuously without being disturbed by electrical noise.

Figure 6:
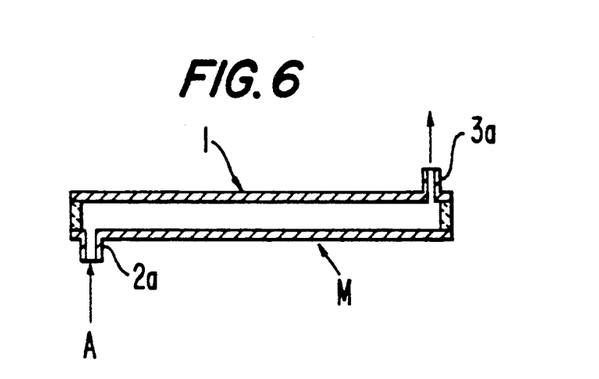
FIG. 6 is a sectional view of a module included in a concentration measuring apparatus in a second embodiment.
Figure 7:
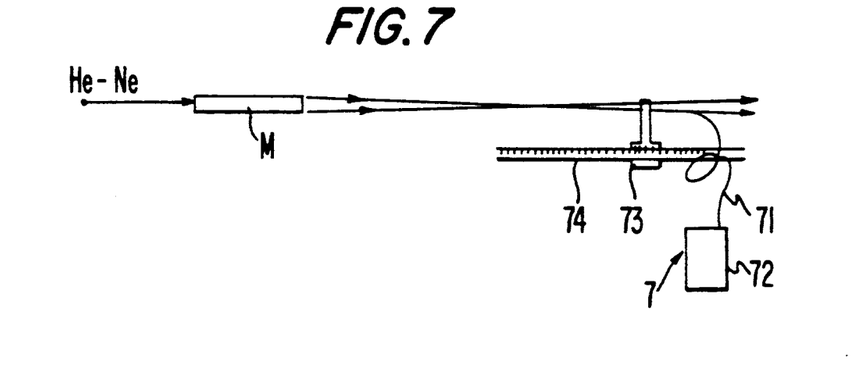
FIG. 7 is a diagrammatic illustration of means for detecting the point of the convergence of light in the second embodiment.
Figure 8:
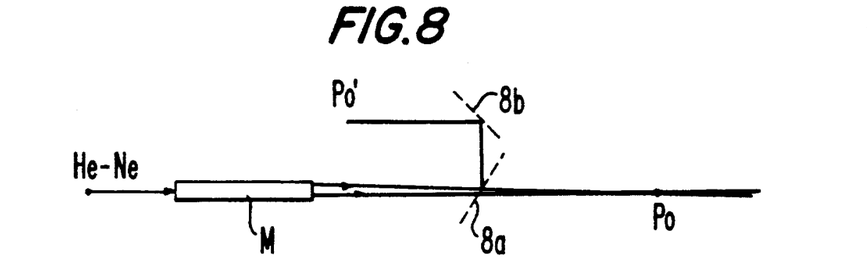
FIG. 8 is a diagrammatic illustration of means for detecting the point of convergence of light employing reflecting mirrors in the second embodiment.

According to a concentration measuring apparatus in a second embodiment as shown in FIG. 6, an inlet port 2a (feed means) and an outlet port 3a (discharge means) are attached directly to a tube 1. As shown in FIG. 7, a converging point detector 7 is disposed to another of the module M. This converging point detector 7 comprises an optical meter 72, which detects luminous flux power, an optical fiber 71 (core diameter of, for example, 50 μm), a holder 73 holding the other end of the optical fiber 71, and a vernier caliper 74 for measuring the position of a point of convergence. The concentration measuring apparatus provided with two reflecting mirrors 8a and 8b inclined at 45° to the optical axis as shown in FIG. 8 forms a concentration measuring apparatus that is particularly compact in construction.

A He-Ne laser beam (exemplary parameters of wavelength 543 nm, power 1 mW) is projected substantially along the axis of the tube 1. The light receiving face of the optical fiber 71 is moved along the optical axis to find a point where the quantity of the He-Ne laser beam received reaches a maximum, namely, a converging point Po of the transmitted light.

Since the concentration and the converging point have a satisfactory linear correlation represented by a straight line having a large gradient as in the first embodiment, the concentration measuring apparatus can accurately, quickly, and continuously measure the concentration in a wide range without being disturbed by electrical noise, and is not susceptible to variations of the luminous intensity of the light source or small bubbles contained in the mixed solution. The concentration measuring apparatus is simple and compact in construction. Particularly, the employment of the reflecting mirrors reduces the dimensions of the concentration measuring apparatus.

The present invention is not limited to the foregoing specific embodiments in its practical application and changes and variations may be made therein without departing from the scope of the present invention, The dimensions, general shape, and material of the tube may be selectively determined so as to meet the object and purpose of use. For example, the tube may be a straight tube or a curved tube. The sectional shape may be circular, square, hexagonal, or elliptical. The tube may have a plurality of parallel pores to flow a mixed solution, namely, a honeycomb type or a lotus root type. The material is not limited to copper, and metal, glass, etc., may be used.

The medium (solvent) used in the mixed solution is not limited to the above mentioned medium. The present invention may be applicable to any mixed solution wherein the light power received, etc., varies and any mixing ratio of mixed solution and the concentration can be detected. For another example, the mixed solution may be water-methanol mixed solution, water-ethyleneglycol mixed solution, etc. Optimum measuring conditions are determined selectively in consideration of the properties of the mixed solution. The number of the solvents of the mixed solution is usually two, but is not limited to two, and may be not less than three, provided that the relation between the concentration of the objective solvent and the quantity of light received can be represented by a finite curve.

The concentration measurement apparatus in the above mentioned embodiment was operated manually for concentration measurement and data processing. However, the concentration measurement apparatus may be operated automatically, and may be provided with a data processing unit, such as a picture processing unit, for moving the light receiving face, and for measuring and recording the measured quantity of light received at a converging point. Ordinarily, a parallel light beam is used that substantially uniformly irradiates the end face of the tube, but the irradiating method is not limited to this method. The diameter of the light beam may selectively determined according to the purpose.

Figure 9:
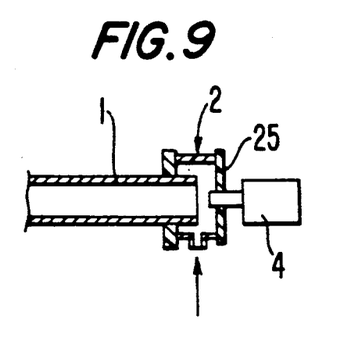
FIG. 9 is an explanatory illustration of a mode in which a light emitting device is joined directly to an outside plate.
Figure 10:
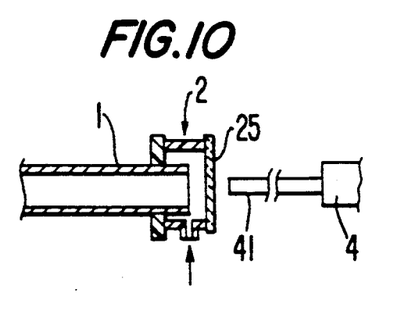
FIG. 10 is an explanatory illustration of a mode in which an end of an optical fiber is disposed opposite to a glass window.
Figure 11:
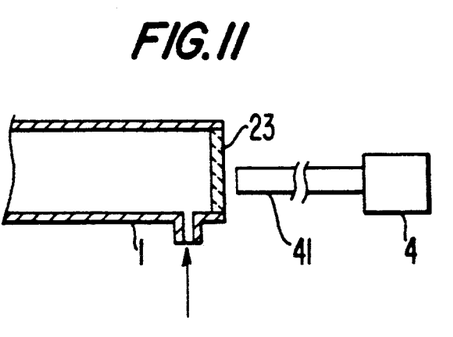
FIG. 11 is an explanatory illustration of another mode in which an end of the optical fiber is disposed opposite to a glass window.
Figure 12:
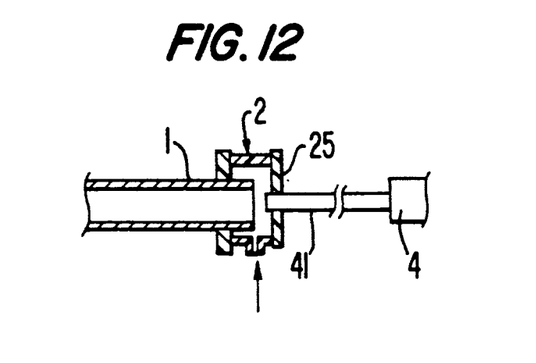
FIG. 12 is an explanatory illustration of a mode in which an end of an optical fiber is intruded into an outside plate.
Figure 13:
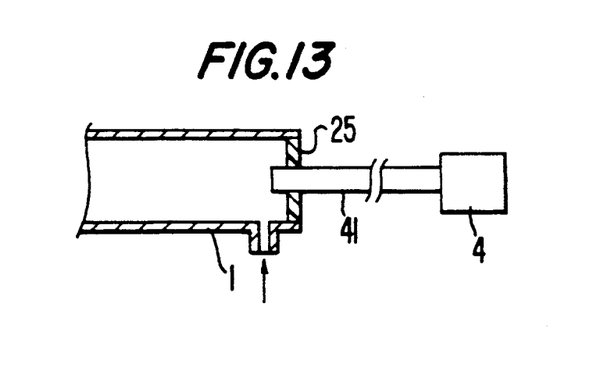
FIG. 13 is an explanatory illustration of another mode in which an end of an optical fiber is intruded into an outside plate.

The length, thickness, material, morphology and arrangement of the optical fiber may selectively determined. The optical fiber may be an optical glass fiber or an optical resin fiber. Optical fibers may be disposed on both sides or on side of the module or tube. This case is convenient for remote control of processes. As shown in FIGS. 10 and 11, the optical fiber may be disposed opposite to a glass window. As shown FIGS. 12 and 13, the optical fiber may be joined directly to an outside plate 25. This outside plate 25 may be made of non-transmitted material or light-transmitted material. The light emitting device may be joined directly to the outside plate 25 as shown FIG. 9.

Although the invention has been described in its preferred forms with a certain degree of particularity, changes and variations thereof are possible. It is therefore to be understood that the scope of the present invention is defined by the appended claims and their equivalents.

What is claimed is:

1. A method for measuring the concentration of an objective solvent in a mixed solution, comprising the steps of:

flowing a mixed solution through a tube having a first end and second a end;

transmitting a light beam through the first end of the tube, through the mixed solution therein, and out of the second end of said tube;

detecting the quantity of light received at the second end of the tube; and determining the concentration of the objective solvent in the mixed solution on a basis that the quantity of light received is dependent on the concentration of the objective solvent in the mixed solution.

2. A concentration measuring method according to claim 1 wherein said step of transmitting light comprises the step of transmitting laser light.

3. A concentration measuring apparatus for measuring the concentration of an objective solvent in a mixed solution comprising:

a tube having a first and second end;

feed means disposed at the first end of the tube for feeding the mixed solution into the first end of said tube, the feed means including a first base, a first glass window for light transmission, and a first cylinder having an inlet port;

discharge means disposed at the second end of the tube for discharging said mixed solution from the second end of said tube, such that the mixed solution flows through the tube;

a light emitting means disposed at the first end of said tube for transmitting a light beam through the tube; and light detecting means disposed at the second end of the tube for receiving the light beam and for measuring the quantity of light received through the mixed solution flowing in said tube.

4. A concentration measuring apparatus according to claim 3, wherein said first cylinder is disposed between said first base and said first glass window, and wherein said light emitting means is disposed opposite to said first glass window.

5. A concentration measuring apparatus according to claim 4, wherein said feed means further comprises an outside plate, said first cylinder being disposed between said first base and said outside plate, and wherein said light emitting means includes a part protruding into said outside plate.

6. A concentration measuring apparatus according to claim 3, further comprising an inlet port in said feed means and an outlet port in said discharge means, said inlet port and said outlet port being attached directly to said tube, and wherein the first glass window for light transmission is attached directly to the first end of said tube, and wherein said light emitting means is disposed opposite to said first glass window.

7. A concentration measuring apparatus for measuring the concentration of an objective solvent in a mixed solution comprising:

a tube having a first and second end;

feed means disposed at the first end of the tube for feeding the mixed solution into the first end of said tube;

discharge means disposed at the second end of the tube for discharging said mixed solution from the second end of said tube such that said mixed solution flows through said tube;

an optical fiber having opposed ends for transmitting light, said optical fiber being attached at one end to said first end of said tube;

a light emitting device connected to the other end of said optical fiber for emitting a light beam through said tube; and light detecting means disposed at said second end of said tube for receiving said light beam, and for measuring the quantity of light received at said second end of said tube through said mixed solution flowing in said tube, and for determining the concentration of said objective solvent from the quantity of light measured.

8. A concentration measuring apparatus according to claim 7, wherein said feed means comprises a first base, a first glass window for light transmission, and a first cylinder having an inlet port, said first cylinder being disposed between said first base and said first glass window, and wherein an end of said optical fiber is disposed opposite to said first glass window.

9. A concentration measuring apparatus according to claim 7, wherein said feed means comprises a first base, an outside plate, and a first cylinder having an inlet port, said first cylinder being disposed between said first base and said outside plate, and wherein one of the ends of said optical fiber is protrudes into said outside plate.

10. A concentration measuring apparatus according to claim 9, wherein said feed means includes an inlet port and said discharge means includes an outlet port, said inlet port and said outlet port being attached directly to the respective ends of said tube, and a first glass window for light transmission attached directly to the first end of said tube, and a second glass window for light transmission attached directly to the second end of said tube, and wherein one of the ends of said optical fiber for transmitting light is disposed opposite to said first glass window.

11. A concentration measuring apparatus according to claim 7, wherein said feed means includes an inlet port and said discharge means includes an outlet port, said inlet port and said outlet port being attached directly to said tube, and an outside plate is attached directly to the first end of said tube, and a glass window for light transmission is attached directly to the second end of said tube, and wherein, one of the ends of said optical fiber for transmitting light protrudes into said outside plate.

12. A concentration measuring apparatus according to claim 7, wherein said light emitting device is a laser.

13. A concentration measuring apparatus according to claim 8, wherein said light emitting device is a laser.

14. A concentration measuring apparatus according to claim 9, wherein said light emitting device is a laser.

15. A concentration measuring apparatus according to claim 10, wherein said light emitting device is a laser.

16. A concentration measuring apparatus according to claim 11, wherein said light emitting device is a laser.

17. A concentration measuring apparatus according to claim 7, wherein a first reflecting mirror and a second reflecting mirror are disposed oppositely at an inclination of 45° to a direction of travel of the light emitted from the second end of said tube, and a direction of light reflected by said second reflecting mirror is substantially parallel and opposite to said direction of travel of said light emitted from said second end of said tube.

18. A method for measuring the concentration of an objective solvent in a mixed solution, comprising the steps of:

flowing a mixed solution through a tube having a first end and a second end;

transmitting a light beam through the first end of the tube, through the mixed solution therein, and out of the second end of said tube;

detecting the diameter of the light beam received at the second end of the tube; and determining the concentration of the objective solvent in the mixed solution on a basis that the diameter of the light beam received at the second end of the tube is dependent on the concentration of the objective solvent in the mixed solution.

19. A method for measuring the concentration of an objective solvent in a mixed solution, comprising the steps of:

flowing a mixed solution through a tube having a first end and a second end;

transmitting a light beam through the first end of the tube, through the mixed solution therein, and out of the second end of said tube;

detecting a point of convergence of the light beam; and determining the concentration of the objective solvent in the mixed solution on a basis that the point of convergence of the light beam is dependent on the concentration of the objective solvent in the mixed solution.

20. A concentration measuring apparatus according to claim 3, wherein said discharge means comprises a second base, a second glass window for light transmission, and a second cylinder having an outlet port, said second cylinder being disposed between said second base and said second glass window.

21. A concentration measuring apparatus according to claim 7, wherein said discharge means comprises a second base, a second glass window for light transmission, and a second cylinder having an outlet port, said second cylinder being disposed between said second base and said second glass window.

* * * * *

UNITED STATES PATENT AND TRADEMARK OFFICE
CERTIFICATE OF CORRECTION

PATENT NO.   :   5,068,542
DATED        :   November 26, 1991
INVENTOR(S)  :   Ando et al.

It is certified that error appears in the above-identified patent and that said Letters Patent is hereby corrected as shown below:

Title, line 4, "CONVERGENT" should read --CONVERGENCE--.
Claim 1, column 6, line 47, "second a end" should read
--a second end--.

Signed and Sealed this

Sixteenth Day of March, 1993

Attest:

STEPHEN G. KUNIN

Attesting Officer            Acting Commissioner of Patents and Trademarks